United States Patent [19]

O'Phelan

[11] Patent Number: 5,312,442

[45] Date of Patent: May 17, 1994

[54] ENERGY DISSIPATION RESISTOR FOR IMPLANTABLE DEFIBRILLATION CIRCUITRY

[75] Inventor: Michael O'Phelan, Roseville, Minn.

[73] Assignee: Cardiac Pacemakers, Inc., St. Paul, Minn.

[21] Appl. No.: 878,537

[22] Filed: May 5, 1992

[51] Int. Cl.$^5$ .............................. A61N 1/39
[52] U.S. Cl. ............................................ 607/5
[58] Field of Search ................... 128/419 D; 338/307–308, 328; 607/5

[56] References Cited

U.S. PATENT DOCUMENTS

| 2,482,316 | 9/1949 | Bocking | 338/328 |
|---|---|---|---|
| 2,521,894 | 9/1950 | Brown | 338/328 |
| 3,654,580 | 4/1972 | Laisi | 338/307 |
| 3,798,542 | 3/1974 | Dempsey | 128/419 D |
| 4,028,657 | 6/1977 | Reichelt | 338/307 |
| 4,164,946 | 8/1979 | Langer | 128/419 D |
| 4,254,775 | 3/1981 | Langer | 128/419 D |
| 4,297,670 | 10/1981 | Solow | 338/308 |
| 4,316,472 | 12/1982 | Mirowski et al. | |
| 4,488,555 | 12/1884 | Imran | |
| 4,566,457 | 1/1986 | Stemple | 128/419 D |
| 5,053,743 | 10/1991 | Mille et al. | 338/307 |
| 5,163,427 | 11/1992 | Keimel | 128/419 D |

Primary Examiner—William E. Kamm
Attorney, Agent, or Firm—Keck, Mahin & Cate

[57] ABSTRACT

An energy dissipation resistor for dissipating electrical energy stored in implantable defibrillation capacitor(s). The resistor comprises a layer of resistive foil sandwiched between two layers of electrically insulative material so as to define a circuitous resistive path. At least two electrically conductive contacts are disposed through one of the insulative layers such that each of the contacts provides an electrically conductive path from the exterior of the energy dissipation resistor to the resistive foil layer enclosed therein. Conductive leads are electrically connected to the conductive contacts and provide a means by which the energy dissipation resistor can be connected to defibrillation circuitry. The energy dissipation resistor can also be formed integrally with a flexible circuit board, a rigid circuit board, a circuitry liner, or a hybrid substrate.

6 Claims, 3 Drawing Sheets

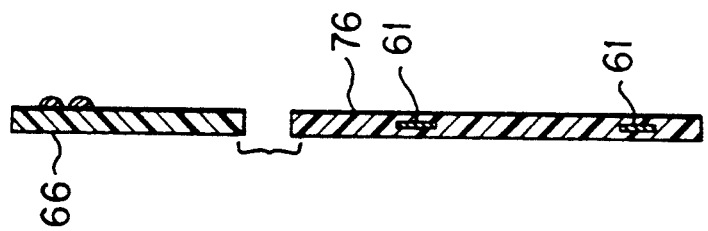
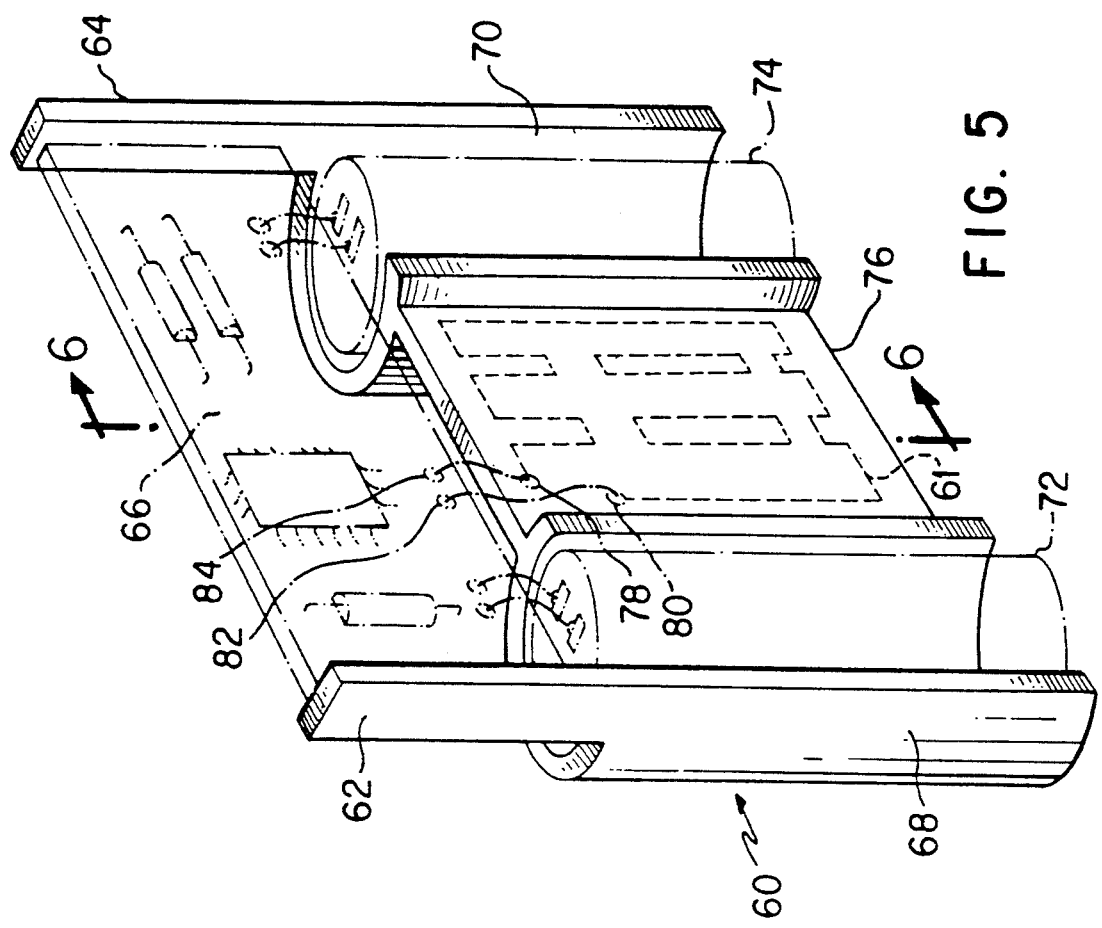

ENERGY DISSIPATION RESISTOR FOR IMPLANTABLE DEFIBRILLATION CIRCUITRY

BACKGROUND OF THE INVENTION

The present invention relates to the art of implantable cardiac defibrillators, and in particular, is related to an energy dissipation resistor capable of efficiently and reliably dissipating energy stored in the capacitor(s) of an implantable cardiac defibrillator.

It is often the desire to dissipate electrical energy stored in defibrillator capacitors, rather than discharging to the heart, by diverting the capacitor voltage to an internal resistor. This is commonly referred to as an "internal dump". See, for example, U.S. Pat. Nos. 4,316,472 and 4,488,555 to Imran and Mirowski, respectively, where internal load resistors are shown. Presently, conventional resistive elements, such as carbon or ceramic resistors, and the like are used to dissipate the energy. Such conventional resistive elements tend to be large and bulky, and therefore difficult to package, often requiring extensive incoming inspection processes to assure that a desired reliability is achieved. In addition, although conventional resistive elements have proven generally effective in practice, worst case testing with multiple shock and internal dump episodes has resulted in heating of the resistive element and occasional destruction thereof.

Some types of implantable defibrillation circuitry are disposed on small, light-weight, and flexible printed circuit boards. Consequently, "board real-estate" becomes increasingly important, as does the size, weight, and flexibility of components mounted thereon. It is, therefore, desirable to minimize the size and weight of individual circuit components, while maximizing their structural flexibility to coincide with that of the flexible circuit board to which they are mounted.

Still other types of implantable defibrillation circuitry are disposed on small, light-weight, but rigid printed circuit boards or ceramic substrates. In such cases, it is usually desirable to conserve "board real-estate" while, at the same time, maintaining structural rigidity in the circuit board.

SUMMARY OF THE INVENTION

It is a primary object of the present invention to solve the above-mentioned problems by providing a thin, light-weight and flexible, or alternatively rigid, energy dissipation resistor for use in implantable cardiac defibrillation circuitry.

It is yet another object of the present invention to provide an energy dissipation resistor having a large surface area so that energy is thereby dissipated rapidly.

A still further object of the present invention is to provide an energy dissipation resistor which can be incorporated into a flexible or rigid circuit board in such a manner that the resistor becomes an integral layer of the circuit board.

To achieve these objects as well as others, an energy dissipation resistor is provided for dissipating stored energy contained in the capacitor(s) or other energy storage devices of an implantable cardiac defibrillator. The dissipation resistor comprises a layer of resistive foil sandwiched between two layers of electrically insulative material. Each insulative layer is bonded by a bonding material to the foil layer, and is sufficiently thin to allow for the rapid dissipation of heat energy from the resistive foil. The resistive foil itself, forms a preferably circuitous resistive path from one electrical contact to another. The two electrical contacts project through at least one of the insulative layers, thereby providing means by which the resistive foil can be electrically connected to a defibrillation circuit. A pair of lead wires may be connected to the electrical contacts of the resistor.

The energy dissipation resistor can be formed integrally as one layer of a flexible or rigid circuit board which frees up space on the outside surfaces of the flexible or rigid circuit board for other components or for down sizing. In addition, multiple layers of the resistive foil and insulative material can be applied so as to form a multi-layered energy dissipation resistor.

Furthermore, by using generally known heat sinking techniques, the energy dissipation resistor can be heat sunk to a housing which contains the defibrillation circuit. As an alternative, the energy dissipation resistor can be molded into a plastic liner inside the housing. Either way, the energy dissipation resistor conforms to the contour of the defibrillation circuit housing or liner, and thus, occupies a minimal amount of usable space therein. The energy dissipation resistor can also be integrally formed with a hybrid substrate.

The above and other objects and advantages of the present invention will become readily apparent from the following description, taken in conjunction with the associated drawings.

BRIEF DESCRIPTION OF THE DRAWINGS

FIG. 5 is a perspective view of a liner for an implantable defibrillation circuit having an integrally formed energy dissipation resistor.

FIG. 6 is a cross section of the liner taken along line 6—6 of FIG. 5.

DETAILED DESCRIPTION OF THE PREFERRED EMBODIMENTS

Figure 1:
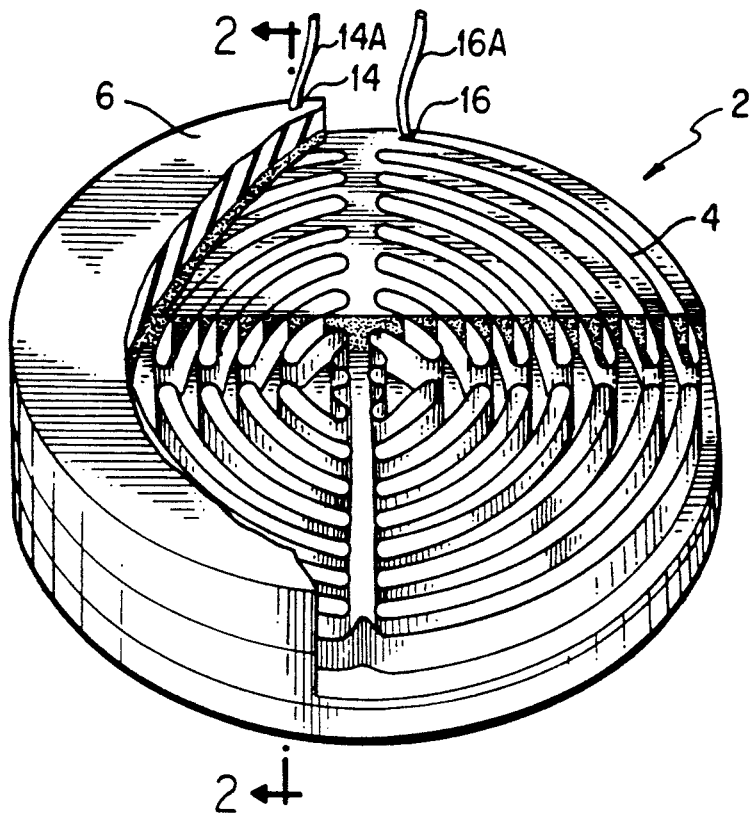
FIG. 1 is a perspective view of the energy dissipation resistor of the present invention.
Figure 2:
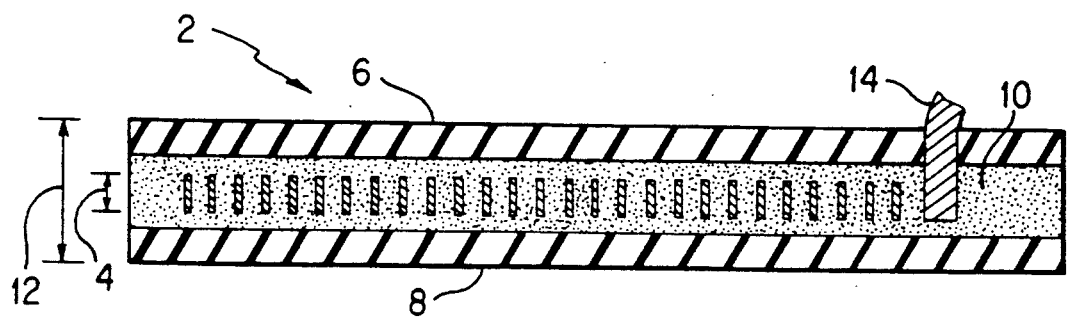
FIG. 2 is a cross section of the energy dissipation resistor taken along line 2—2 of FIG. 1.

With reference to FIGS. 1 and 2, an energy dissipation resistor 2 is shown comprising a foil resistive layer 4 sandwiched between two layers 6 and 8 of electrically insulative material. The foil resistive layer 4 is joined to the insulative layers 6 and 8 by a bonding material 10. In addition to forming a layer of electrically insulative material on each side of the resistive foil layer 4, the layers 6 and 8 allow for the rapid dissipation of thermal energy from the resistive foil 4.

Various materials may be used to construct the resistor 2. Preferably, the resistive foil 4 is comprised of 70 - 30 cupro-nickel (70% copper and 30% nickel); the insulative layers 6 and 8 comprised of "KAPTON", "MYLAR" OR "NOMEX" (all commercially available from Dupont); and the bonding material 10 comprised of "PYRALUX" or "TEFLON" (also commercially available from Dupont).

The energy dissipation resistor 2 is constructed with a thin cross section 12 but large surface area so that dissipation of thermal energy is maximized. In addition, the energy dissipation resistor 2 further comprises two electrical contacts 14 and 16 which are electrically connected to the foil resistive layer 4 and appear through one of the insulative layers 6 or 8. The electrical contacts 14 and 16 are preferably plated with tinned copper, nickel, 67/37 silver/lead, or alternatively, a conductive epoxy. The energy dissipation resistor 2 can also be equipped with a pair of electrically conductive leads 14A and 16A, each lead extending from one of the contacts 14 and 16. The conductive leads 14A and 16A allow the energy dissipation resistor 2 to be located apart from yet be electrically connected to a discharge circuit.

As can be seen most clearly in FIG. 1, the foil layer 4 of the energy dissipation resistor 2, is constructed so as to define a circuitous resistive path from electrical contact 14 to electrical contact 16, the exact length of this path being selectively chosen to achieve a desired total resistance from contact 14 to contact 16 of the resistor. By increasing this path length, higher total resistance values are achieved between the contacts 14 and 16. Lower resistance values, on the other hand, result from decreasing the path length.

One particular application of the energy dissipation resistor 2 relates to the discharging of defibrillation capacitors or other energy storage devices in an implantable cardiac defibrillator. For this purpose, an energy dissipation resistor has been created having a surface area between 2 in.$^2$ and 4 in.$^2$; a pair of insulative layers 6 and 8 each being between 0.0005" and 0.001" thick; a foil resistive layer 4 between 0.0006" and 0.0007" thick; and a bonding material between 0.0005" and 0.001" thick on each side of the foil resistive layer 4. The foil resistive layer 4 defines a resistive path between 170" and 250" long and between 0.004" and 0.010" wide, the exact length of the resistive path being selectively chosen to achieve a desired total resistance between 850 $\Omega$ and 1150 $\Omega$.

Figure 3:
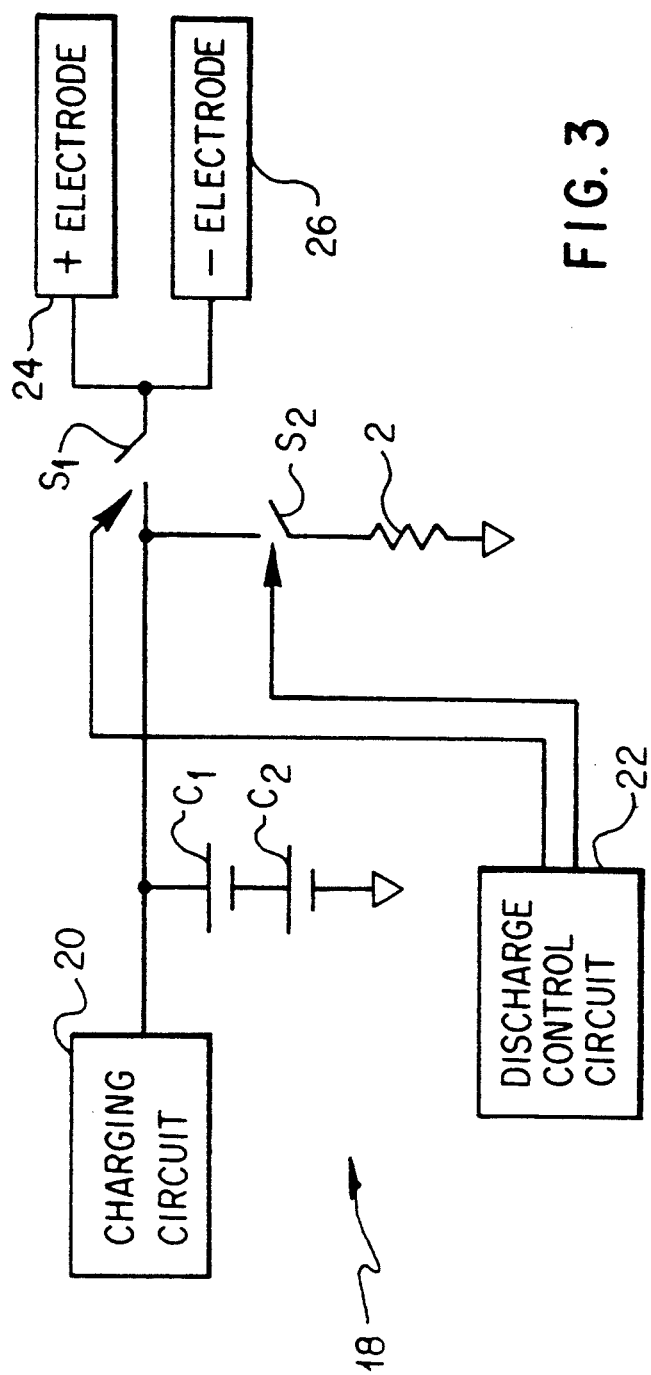
FIG. 3 is a schematic illustration of an implantable cardiac defibrillation circuit which utilizes the energy dissipation resistor of the present invention.

An exemplary cardiac defibrillation circuit 18 is illustrated schematically in FIG. 3. The defibrillation circuit 18 comprises a charging circuit 20, a discharge control circuit 22, two series connected defibrillation capacitors C1 and C2, two switches S1 and S2, a pair of electrodes 24 and 26, and the energy dissipation resistor 2. During operation, the charging circuit 20 provides electrical energy to the defibrillation capacitors C1 and C2 which, in turn, store the electrical energy for future discharge. The discharge control circuit 22 then controls whether the capacitors C1 and C2 should be discharged through a patient via the electrodes 24 and 26 or through the energy dissipation resistor 2. This determination is made based on various criteria which may be analyzed by a microprocessor, not shown. Once such a determination is made, the discharge control circuit 22 causes the appropriate switch S1 or S2 to be closed, thereby closing a circuit through either the electrodes 25 and 26 or the energy dissipation resistor 2. More specifically, if the capacitors C1 and C2 are to be discharged through the patient via the electrodes 24 and 26, switch S1 is closed. Otherwise, switch S2 is closed, allowing the capacitors C1 and C2 to be discharged through the energy dissipation resistor 2. This is known as an "internal dump", and is often used to divert the capacitor voltage when an arrhythmia has reverted or when it is otherwise desired not to shock the heart of a patient after the capacitors have been charged, as when the implanted device is being tested for remaining life of the batteries, etc. In addition, this internal dump can be used when the capacitors C1 and C2 need to be "formed" approximately every two months. Forming can be accomplished using both auto-form and manual-form options.

Figure 4:
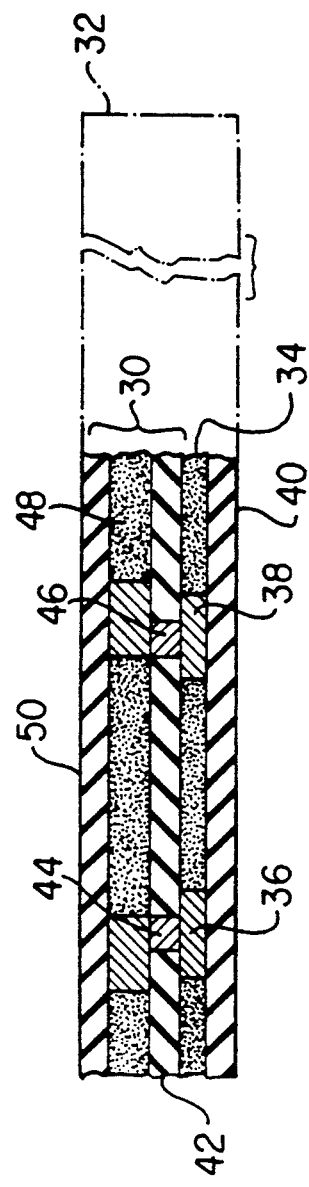
FIG. 4 is a cross-sectional illustration of an energy dissipation resistor integrally formed in a flexible circuit board.

Referring to FIG. 4, the energy dissipation resistor indicated generally at 30 is shown to be formed integrally with a flexible circuit board 32. In particular, the circuit board 32 comprises a layer 34 of electrically conductive circuit lines 36 and 38 between two layers 40 and 42 of insulative material, one of the layers 42 having a pair of conductive contacts 44 and 46 disposed therein. The energy dissipation resistor 30 comprises a layer of resistive foil 48 adjacent the insulative layer 42 which contains the contacts 44 and 46 so that the contacts 44 and 46 form an electrically conductive path from their respective circuit lines 36 and 38 to the resistive foil layer 48. An insulative layer 50 covers the other surface of the resistive foil layer 48. The individual layers 34, 40, 42, 48 and 50 are bonded to one another by a bonding material 51, as is well known in the art.

When the circuit board 32 is used for implantable cardiac defibrillation circuitry, each layer 40, 42, and 50 of insulative material is between 0.0005" and 0.001" thick; the layer 34 of electrically conductive circuit lines is between 0.0014" and 0.0028" thick; and the layer of resistive foil 48 is between 0.0006" and 0.0007" thick. Sandwiched between each adjacent layer, the bonding material is between 0.0005" and 0.001" thick. The foil resistive layer 48 again defines a resistive path 53 approximately between 170" and 250" long and between 0.004" and 0.010" wide, the exact length of the resistive path 53 being selectively chosen to achieve a desired total resistance between 850 $\Omega$ and 1150 $\Omega$. The resulting flexible circuit board has an overall thickness of approximately 0.005".

The circuit board and integrally formed dissipation resistor can be formed using conventional techniques known to the art of printed circuit board manufacturing. Etching techniques, for example, can be used by first attaching the resistive foil layer 48 to a film substrate using adhesive material such as "Pyralux" or "Teflon". The adhesive material is then cured by methods generally known, while "artwork" is created representative of a desired resistive path in the resistive foil layer 48. Next, in accordance with the "artwork," a photo-resist is selectively applied to the resistive layer 48, which photo-resist prevents the removal of predetermined portions of the resistive foil layer 48 by a subsequently applied etchant. The etchant, once applied, removes the undesired portions of the resistive layer 48 thereby defining a predetermined resistive path 53. By repeating the foregoing technique, subsequent layers can be applied to thereby form a multi-layer energy dissipation resistor.

The circuit board and integrally formed energy dissipation resistor can also be manufactured using conventional methods of electro-depositing foil material. That is, the foil layer defining the resistive path 53 can be formed by selectively electro-depositing the foil onto a base or substrate layer of electrically insulative material. Preferably, the electro-deposited foil has a thickness of between 0.0006" and 0.0007".

It is well understood that numerous other modifications of the present invention will become subsequently apparent to those skilled in the art. One modification involves the molding of the energy dissipation resistor into a liner of an implantable defibrillation circuit.

FIGS. 5 and 6 illustrate an example of such an embodiment, wherein a plastic liner 60 for defibrillation circuitry has a circuitous resistive path 61 molded therein, which resistive path 61 defines an energy dissipation resistor in accordance with the present invention. Specifically, the plastic liner 60 comprises two elongated support arms 62 and 64 for supporting a defibrillation circuit board 66; two cylindrical support members 68 and 70 for receiving and supporting a pair of capacitors 72 and 74; a planar center member 76 for supporting a pair of adhesively attached rectangular batteries (not shown); and a circuitous resistive path 61 molded inside the plastic of the planar center member 76. The resistive path 61 defines an energy dissipation resistor which is integrally formed within the plastic liner 60. The circuitous resistive path is electrically connected to the circuit board 66 via a pair of electrically conductive contacts 78 and 80 and leads 82 and 84. In practice, the combination of the liner 60, the circuit board 66, and the two capacitors 72 and 74, typically measures 3 inches in height, 3 inches in width, and 0.75 inches in thickness. Preferably, the planar center member 76 has a surface area of between 2 in$^2$ and 4 in$^2$, with an overall thickness of approximately 0.005".

It is further understood that the previously mentioned electro-depositing techniques can also be utilized to deposit the energy dissipation resistor of the present invention directly onto a plastic liner for a defibrillation circuit.

In addition, the energy dissipation resistor can be incorporated into, or printed onto, an analog or digital hybrid substrate. Hybrid substrates typically comprise a rigid ceramic or cofire ceramic material having favorable electrical properties, such as high resistance to dielectric breakdown. In practice, the resistor can be incorporated into the substrate using any of the foregoing arrangements or methods for incorporating the resistor into a flexible circuit board.

The foregoing description is by way of example only and is not intended to limit the present invention in any way except as set forth in the following claims.

I claim:

1. A defibrillator circuit board having an integrally formed energy dissipation resistor for implantable defibrillation circuitry, said circuit board comprising:
   an elongate resistive path formed of electrically resistive foil and formed into a resistive path layer;
   first and second layers of electrically insulating material on opposite sides of said resistive path layer;
   at least two electrically conductive contacts providing at least two electrically conductive paths through said second layer of electrically insulating material to electrically connect with said resistive path;
   a layer of electrically conductive circuit lines adjacent to said second layer of electrically insulating material, said circuit lines including means for connecting said elongate resistive path to a remainder of said implantable defibrillation circuitry, at least two of said circuit lines being electrically connected to said at least two electrically conductive contacts; and
   a third layer of electrically insulating material adjacent said layer of electrically conductive circuit lines.

2. The circuit board of claim 1, and further comprising bonding material for bonding adjacent layers of the circuit board to one another.

3. The circuit board of claim 2, wherein said bonding material is comprised of "PYRALUX".

4. The circuit board of claim 2, wherein said bonding material is comprised of "TEFLON".

5. The circuit board of claim 1, wherein the electrically resistive foil is comprised of cupro-nickel.

6. The circuit board of claim 1, wherein the electrically insulating material is comprised of "KAPTON".

* * * * *